United States Patent
Hirt et al.

(10) Patent No.: US 8,956,334 B2
(45) Date of Patent: Feb. 17, 2015

(54) ENTERAL FEED CUP

(71) Applicants: Douglas Hirt, Seneca, SC (US);
Michele Horton, Martinez, GA (US)

(72) Inventors: Douglas Hirt, Seneca, SC (US);
Michele Horton, Martinez, GA (US)

( * ) Notice: Subject to any disclaimer, the term of this patent is extended or adjusted under 35 U.S.C. 154(b) by 0 days.

(21) Appl. No.: 13/938,740

(22) Filed: Jul. 10, 2013

(65) Prior Publication Data

US 2014/0018747 A1 Jan. 16, 2014

Related U.S. Application Data

(60) Provisional application No. 61/670,297, filed on Jul. 11, 2012.

(51) Int. Cl.
*A61M 5/00* (2006.01)
*A61J 15/00* (2006.01)
*A61J 9/00* (2006.01)
*A61J 9/06* (2006.01)

(52) U.S. Cl.
CPC ............. *A61J 15/0026* (2013.01); *A61J 9/00* (2013.01); *A61J 9/06* (2013.01); *A61J 2009/0684* (2013.01)
USPC ........................................................ 604/257

(58) Field of Classification Search
CPC ......... A61J 1/10; A61J 1/2093; A61J 1/1475; A61J 2001/2024; A61J 1/12; A61J 1/2089; A61J 2001/201; A61J 1/05; A61J 1/1406; A61J 2205/30; A61J 15/00; A61J 1/1462; A61J 1/18; A61J 1/2096
USPC ......... 604/257, 261, 403, 407, 409, 413–415; 215/200, 329, 393
See application file for complete search history.

(56) References Cited

U.S. PATENT DOCUMENTS

| | | | | |
|---|---|---|---|---|
| 1,574,575 | A * | 2/1926 | Harmon et al. | 604/261 |
| 2,923,297 | A * | 2/1960 | Holt | 604/251 |
| 3,134,494 | A * | 5/1964 | Quinn | 215/11.3 |
| 3,165,241 | A * | 1/1965 | Curry | 222/490 |
| D236,919 | S * | 9/1975 | McPhee | |
| 3,938,519 | A * | 2/1976 | McPhee | 604/404 |
| D242,018 | S * | 10/1976 | Gargione | |
| D284,033 | S * | 5/1986 | Brodsky | D24/117 |
| 4,886,504 | A * | 12/1989 | Arvidson et al. | 604/257 |
| D367,325 | S * | 2/1996 | Duggan et al. | D24/121 |
| 5,782,383 | A * | 7/1998 | Robinson | 222/81 |
| 6,752,790 | B2 * | 6/2004 | Coombs | 604/251 |
| 7,611,502 | B2 * | 11/2009 | Daly | 604/411 |
| 7,666,171 | B2 * | 2/2010 | Mombrinie et al. | 604/257 |
| 7,799,008 | B2 * | 9/2010 | Hendricks | 604/403 |
| 7,931,629 | B2 * | 4/2011 | Romano | 604/317 |
| D656,403 | S * | 3/2012 | Bernstein et al. | D9/529 |
| D656,690 | S * | 3/2012 | Tu | D30/127 |
| 8,231,597 | B2 * | 7/2012 | Knight | 604/415 |

(Continued)

FOREIGN PATENT DOCUMENTS

WO WO 2011/071729 6/2011

*Primary Examiner* — Nicholas Lucchesi
*Assistant Examiner* — Diva K Chander
(74) *Attorney, Agent, or Firm* — Dority & Manning, P.A.

(57) ABSTRACT

A large enteral feed cup large enough to contain an amount of fluid suitable for a single dose (nutrition and/or medicines) is described. The enteral feed cup can be free-standing on the proximal end so as to facilitate filling via an opening on the distal end. The distal end includes a resealable closure for an opening that can be quite large and thus can be easily filled with less chance of spillage. The free-standing design of the enteral feed cup can also allow for the cup to be used in any convenient location.

20 Claims, 6 Drawing Sheets

(56) References Cited

U.S. PATENT DOCUMENTS

| | | | |
|---|---|---|---|
| 8,628,509 B2* | 1/2014 | Kropczynski et al. | 604/414 |
| 2004/0011760 A1 | 1/2004 | Schupp et al. | |
| 2004/0215148 A1* | 10/2004 | Hwang et al. | 604/187 |
| 2010/0004629 A1 | 1/2010 | Dolhun | |
| 2010/0084362 A1* | 4/2010 | Letchinger et al. | 215/200 |
| 2010/0204669 A1 | 8/2010 | Knight | |
| 2010/0262114 A1 | 10/2010 | Brandenburger et al. | |
| 2011/0118676 A1 | 5/2011 | Kropczynski, Jr. et al. | |
| 2012/0065608 A1* | 3/2012 | Costello et al. | 604/403 |
| 2012/0211461 A1* | 8/2012 | Windmiller | 215/235 |
| 2013/0331810 A1* | 12/2013 | Bazala et al. | 604/414 |
| 2014/0018747 A1* | 1/2014 | Hirt et al. | 604/257 |

\* cited by examiner

ENTERAL FEED CUP

CROSS REFERENCE TO RELATED APPLICATION

The present application claims filing benefit of U.S. provisional patent application Ser. No. 61/670,297 filed on Jul. 11, 2012, which is hereby incorporated by reference in its entirety.

BACKGROUND

Certain medical conditions require that individuals feed using direct enteral nutrition, also referred to as use of feeding tubes. It is estimated that in excess of 350,000 persons of all ages use enteral nutrition in the home setting. Many of these conditions allow the individual to maintain an active lifestyle that can include career, schooling, active hobbies, and even physically demanding sports.

Unfortunately, the current method of gravity bolus (batch) feeding is not consistent with dynamic lifestyles; primarily as it is neither practical nor portable. Many individuals are bolus tube fed multiple (5+) times per day by use of a 2 ounce syringe that is filled and allowed to gravity drain into the feeding tube. When the 2 ounces are emptied, another 2 ounces are poured into the syringe. This process is repeated until a full feed (e.g., about 8 ounces) is administered. Problems with existing systems include the size of the syringe, which has a small mouth making it difficult to fill and also requires several refills for each feed. In addition, syringes are not designed for pre-loading, storage, or transport for convenient feeding away from home as once filled, the syringe must be held upright to prevent spilling of contents.

What are needed in the art are enteral feed cups that can provide more convenient and easier feeding for individuals. For example, an enteral feed cup that can be self-standing to allow for filling, storage, and use in any location would be of great benefit.

SUMMARY

According to one embodiment disclosed is an enteral feed cup that can be portable, reusable, and large enough to provide a complete feed without the need for refilling during a feeding cycle. For example, the enteral feed cup can include a proximal end and a distal end and can define a volume in a body so as to contain suitable fluid for a complete feeding cycle. The proximal end includes a catheter tip discharge and the distal end defines an opening via which the reservoir may be filled. The enteral feed cup also includes a closure that resealably seals the distal end with a water-tight seal.

According to one embodiment, the enteral feed cup includes structures, e.g., outer wall extensions, a removable cap, etc. such that the enteral feed cup can freely stand on the proximal end, i.e., the feed cup can freely stand on a surface with the distal end farther from the surface than the proximal end.

According to another embodiment, the enteral feed cup can be formed so as to have a larger cross sectional dimension at the distal end of the reservoir as compared to the proximal end. The wider distal end can allow for the enteral feed cup to be securely held in a bracket (e.g., a self-standing bracket) so as to provide for more convenient and portable use of the enteral feed cup.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which:

FIG. 8 illustrates an enteral feed cup and a stand for the enteral feed cup in exploded view (FIG. 8A) and following assembly (FIG. 8B).

FIG. 9 illustrates an enteral feed cup and a stand for the enteral feed cup in exploded view (FIG. 9A) and following assembly (FIG. 9B).

Other objects, features and aspects of the subject matter are disclosed in or are obvious from the following detailed description.

DETAILED DESCRIPTION OF PREFERRED EMBODIMENTS

Reference will now be made in detail to various embodiments of the disclosed subject matter, one or more examples of which are set forth below. Each embodiment is provided by way of explanation of the subject matter, not limitation of the subject matter. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment. Thus, it is intended that the present disclosure cover such modifications and variations as come within the scope of the appended claims and their equivalents.

In general, disclosed herein are enteral feed cups that can provide improved use for Individuals. For example, an enteral feed cup can be large enough to contain an amount of fluid suitable for a single feed (containing nutrients and/or medicines), and such need not be refilled during a feeding cycle. In addition, the enteral feed cup can be designed so as to be free-standing with the proximal end of the cup nearer the surface upon which the cup is standing, the proximal end including the catheter tip discharge. The free-standing ability of the cup can allow for the cup to be filled at the distal end. The distal end can also include a resealable closure for an opening that can be sufficiently large and thus can be easily filled with less chance of spillage. The free-standing design of the enteral feed cup can also allow for the cup to be used in any convenient location.

The size of the enteral feed cup can allow for a single batch of nutrition to be conveniently prepared, stored and delivered in a single container. Current protocol generally requires that users mix in a first bottle, then measure in another, and then pour multiple times into the syringe. The disclosed enteral feed cup can provide all of these functions in a single unit. Other benefits are numerous and include increased portability, improved convenience, and fewer spills. The enteral feed cup can facilitate pediatric night feedings, can improve storage and transportation, can provide better accommodation of backflow, lessens potential for stomach air, and creates less conspicuous public feedings. The enteral feed cup can also enhance both safety and dose accuracy and can alleviate daily stresses associated with tube feeding.

Figures 1, 2, 3:
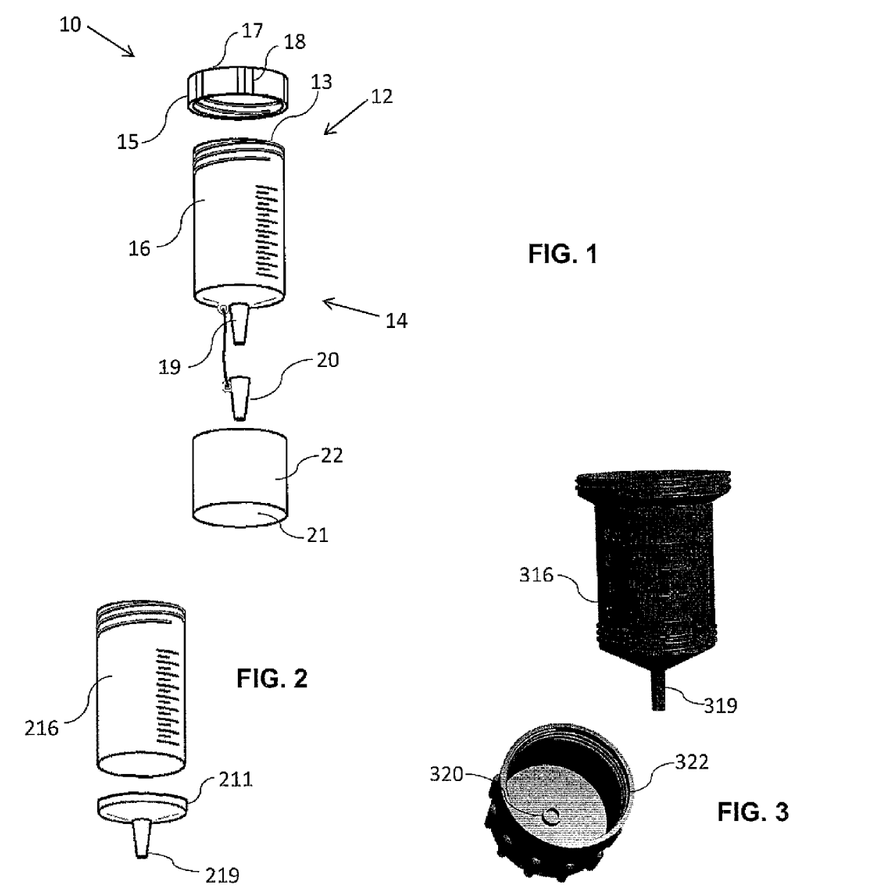
FIG. 1 illustrates one embodiment of an enteral feed cup as disclosed herein.
FIG. 2 illustrates a two-piece body of an enteral feed cup as disclosed herein.
FIG. 3 illustrates a perspective view of a cap and an enteral feed cup as may be utilized in conjunction with the cap.

FIG. 1 illustrates one embodiment of the enteral feed cup 10. The enteral feed cup 10 includes a distal end 12 and a proximal end 14. The distal end 12 includes an opening 13 through which the enteral feed cup 10 can be filled. The opening 13 can generally be large enough so as to facilitate filling of the feed cup 10 and avoid spilling. For example, the opening 13 can be greater than about 0.5 inch in diameter, greater than about 1 inch in diameter, or greater than about 2 inches in diameter. For instance the diameter of the opening 13 can be from about 2 inches to about 4 inches, or from about 2.5 inches to about 3.5 inches.

The distal end 12 of the enteral feed cup 10 also includes a closure 15 that can cover the opening 13 of the cup. In this particular embodiment, the closure 15 is a screw-on lid, but any suitable closure can be utilized that can provide a water-tight seal for the feed cup 10 so as to prevent spillage during storage, transport, and/or use. To enhance seal tightness between the closure 15 and the body 16 of the cup 10 a gasket (not shown) as is generally known in the art can be included. The closure 15 can be flat on the top 17, as shown, such that the cup 10 can freely stand on the distal end 12, for instance during storage.

The closure 15 can include added features to ease the use of the enteral feed cup 10. For example, the closure 15 can include features 18 formed at the side of the closure 15 that can ease closure removal and tightening. Features 18 can also prevent rolling of a round cup when the cup 10 is laid on the side. The form of the features 18 is not particularly limited. For instance, the features 18 can extend above the surface of the closure to form a series of ridges around the closure, can be cut into the surface of the closure, or can be in line with the rest of the surface. The features 18 may be formed of the same material as the rest of the closure 15 or may be formed of a different material. For example, the features may be formed of a softer material, such as a soft elastomer, that can improve an individual's grip and ease tightening and loosening of the closure. The closure 15 may include a plurality of features 18 that extend around the closure 15 or may include a single feature. The inclusion of features 18 can be particularly beneficial for individuals who may otherwise encounter difficulty with creating and breaking the water-tight seal between the closure 15 and the body 16 of the feed cup, such as the elderly.

Closure 15 can be removably attached to the body 16 of the enteral feed cup 10. The body can be formed of a size so as to contain adequate fluid volume for a full feeding cycle as well as for medicine dosings, e.g., greater than about 1 fluid ounce, greater than about 4 fluid ounces, or greater than about 6 fluid ounces. For example, the body 16 can contain a volume of between about 4 fluid ounces and about 24 fluid ounces, for instance between about 6 fluid ounces and about 16 fluid ounces. For instance, the body 16 can be from about 3 to about 10 inches in length, for instance from about 4 to about 8 inches in length. Due to the size of the body 16, a user can measure a fully feeding amount of nutritional material into the cup 10 prior to use and, if desired store the nutritional material for later use. The size of the body 16 can also allow the enteral feed cup 10 to be stored in a convenient location prior to use such as, for example, a lunchbox, a car cup holder, and so forth. The flat top 17 at the distal end 12 of the cup can allow for storage on the distal end, which can prevent clogging or settling of the feeding material in the catheter tip discharge 19.

The large size of the body 16 can eliminate refilling of the cup 10 during a feed cycle. Current methods, in which a syringe must be refilled several times during a single feeding cycle, can lead to measurement errors, as one may lose count of the amount of nutritional material that has been fed to the syringe. In addition, according to current practice additional nutritional material is added to the syringe while nutritional material is being delivered from the catheter end of the syringe, which can also lead to errors in determining the total amount of fluid fed to the individual during the feeding cycle. The larger size of the body 16 of the feed cup 10 can eliminate the need for refilling during a feeding cycle, thereby ensuring the correct measurement in the amount of nutritional material delivered during the feeding cycle. The size of the body 16 can also prevent the introduction of air into the feeding tube, and thence the individual's stomach, during a feeding cycle. For instance refilling of the container during use as is required for small enteral feeding syringes that are currently used can introduce air into the feeding tube.

Nutritional material that can be placed in the enteral feed cup 10 can be either liquid or solid, as desired. For example, in one embodiment a pre-formed liquid nutritional material can be placed in the body 16 of the feed cup 10. According to another embodiment, a solid nutritional material, for instance a dry powdered drink mix can be located in the body 16 of the feed cup 10 and then prior to use a liquid, e.g., water or milk, can be added to the powder to form the liquid feeding material. This can allow for pre-measuring of the dry powder into the feed cup at a different time than the liquid, which can permit a user increased mobility with the nutritional material, for instance when refrigeration is not available prior to use.

In one embodiment, the body 16 can be of a size so as to accommodate a full feeding cycle of liquid nutritional material, e.g., about 8 fluid ounces, and can also provide for head space area above the liquid, for instance greater than about 1 fluid ounce of head space, such as from about 2 fluid ounces to about 4 fluid ounces of head space. The inclusion of additional volume for head space in the enteral feed cup 10 can improve accommodation of backflow during use of the device. For example, coughing, sneezing, and even laughter can cause backflow through a feeding tube. Head space in the feed cup 10 during use can accommodate tube backflow situations. To improve backflow accommodation, the closure 15 may also be loosely attached to allow some air flow in and out of the cup's headspace 10 during use. This can also prevent splattering that is often associated with backflow.

The body 16 of the cup 10 may be marked or scored with liquid level readings, as shown, and/or other markings, such as "For Enteral Use Only" and/or "Not for IV Use." Such markings may be formed in to the body 16 at the time of molding or may be added to the surface of the body, as through printing, adhesion, or so forth, according to standard practice.

The proximal end 14 of the enteral feed cup 10 can include a catheter tip discharge 19. The catheter discharge tip 19 can connect to the feeding tube according to any standard methodology including friction fit, snap locks, screw threads, etc. The catheter tip discharge can be of a size and shape to be directly or indirectly connectable to a feeding tube as is generally known in the art. For instance, the catheter tip discharge can, be of a size and shape to be connected to a feeding tube extension set that can then be connected to the feeding tube. Of course, any suitable design for connection between the body 16 that can hold the nutrition and/or medicine and an extension tube (or other device for enteral feeding) can alternatively be utilized, and the present disclosure is not limited to any specific tip or connection design. In turn, the extension tube can be connectable to a surgically implantable gastronomy tube as may be utilized to maintain enteral nutrition for extended periods of time. In another example, the catheter discharge tip 19 may be connectable to a jejunostomy tube that bypasses the stomach and provides nutritional material directly into the intestines. Nasogastric tubes as are typically used on a short term basis and feed the stomach via the nose may also be used in conjunction with the enteral feed cup 10. Any other feeding tube type, either surgically implanted or not implanted may alternatively be utilized in conjunction with the enteral feeding cup.

The portion of the enteral feed cup that includes the catheter tip discharge can be integral to the body or can be separable, as desired. For example, as illustrated in FIG. 2, an enteral feed cup body 216 can include a separable portion 211 that includes the catheter tip discharge 219. The separable portion can be attachable to the body 216, for instance by use of threads, a snap-on mechanism, or a friction fit, so as to form a water-tight seal between the body 216 and the portion 211. A separable portion 211 can be useful for reusable feed cups, as it can allow for quick and thorough cleaning of the catheter tip discharge 219.

Referring again to FIG. 1, the enteral feed cup 10 can also include a catheter tip cover 20 that can form water-tight seal over the catheter discharge tip 19 so as to prevent leakage of the contents of the enteral feed cup 10, for instance during storage and/or transport. Tip cover may be attached to the proximal end 14 of the feed cup 10 as illustrated in FIG. 1 so as to prevent loss or may be separable, as desired.

The enteral feed cup also includes a structure 22 that can define a flat surface 21 upon which the enteral feed cup 21 can freely stand on the proximal end. For instance, in the embodiment of FIG. 1 the structure 22 is a removable cap that can fit over the catheter discharge tip 19. The free standing ability of the enteral feed cup 10 by use of the structure 22 can be particularly beneficial for filling the body 16 of the feed cup 10. For example, it is a relatively simple matter to stand the feed cup 10 on the surface 21 of the structure 22, remove the closure 15 from the distal end 12 of the feed cup 10 and fill the body 16 with a nutritional material. Upon sealing the closure 15, the feed cup can be stored prior to use, for instance by standing the feed cup 10 on the surface 17 of the closure 15, so as to avoid settling of nutritional material in the catheter discharge tip during storage.

According to one embodiment illustrated in FIG. 3, the catheter tip cover may be integrated with the structure upon which the feed cup can stand on the proximal end. For example, as shown in FIG. 3, the structure 322 is a removable cap, the catheter tip cover 320 can be integral with the cap 322, and when the cap 322 is attached to the body 316, the catheter tip cover 320 can be attached to the catheter discharge tip 319.

Figure 4:
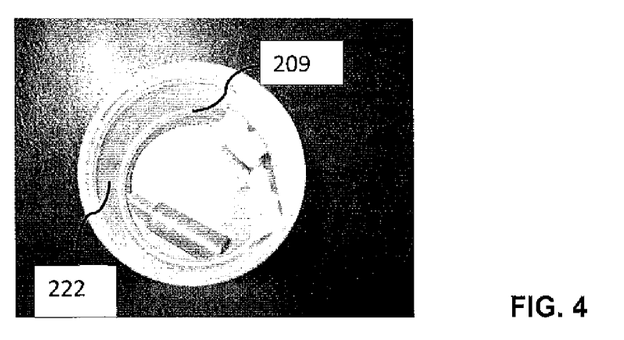
FIG. 4 illustrates a cap as may be utilized to carry a tube extension set for use with an enteral feed cup.

The enteral feed cup can be utilized in conjunction with a tube extension set, as is known in the art. In one embodiment illustrated in FIG. 4, the structure can be in the form of a cap 222. Beneficially, the cap 222 can be of a size so as to provide a safe sanitary storage for a tube extension set 209, for instance a coiled tube extension set. This design can provide a safe, sanitary storage location for the tube extension set that can ease carrying and storage of the enteral feed cup. For example, following manufacturing of the enteral feed cup as well as following cleaning of the enteral feed cup following use, the tube extension set 209 can be coiled inside of the cap 222 as illustrated in FIG. 4. The cap 222 can then be attached to the body of the feed cup. This can completely enclose the tube extension set, protecting it from unsanitary conditions prior to utilization. This feature can greatly ease use of the cup. For instance the entire feed cup including the tube extension set can be transported as a single container without the need to carry the separate components (e.g., the feed cup and the tube extension set) in separate sanitary containers.

Figure 5:
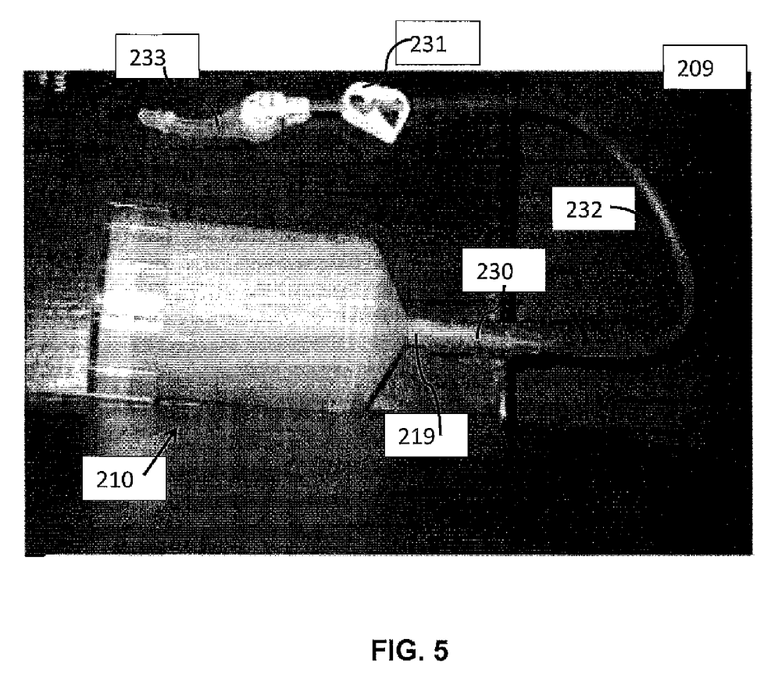
FIG. 5 illustrates an enteral feed cup following assembly with a tube extension set.

As illustrated in FIG. 5, at the time of use, the tube extension set 209 may be removed from the handy carrying location within the cap 222 and attached to the discharge tip 219 of the enteral feed cup 210. The tube extension set 209 may be any suitable size and may be made of any suitable material and may have various combinations of elements. For instance, the tube extension set 209 can include an adapter 230, clamp 231, tubing 232, and connection member 233 as are generally known. The adapter can have a first end configured to connect to the catheter tip discharge 219 and a second end configured to connect to tubing 232. The first end may connect to the catheter tip discharge 219 in any suitable manner. A clamp 231 may be any suitable clamp such as a roller clamp or a slide clamp. The tubing 232 may be made of any suitable material and may have any suitable width, length and thickness. In some embodiments, the tubing 232 may be made of plastic, polyurethane or silicone. The connection member can be adapted for attachment to a feeding tube as is known.

Referring again to FIG. 1, the enteral feed cup 10 can be disposable, designed for a single use, or may be reusable. The specific materials utilized to form the enteral feed cup 10 can be selected based upon this as well as other aspects of the feed cup. In general, however, the various components of the enteral feed cup 10, e.g., the closure 15, the body 16, the structure 22, etc. can be formed of a durable, relatively rigid material that can be conveniently transported and used for storage of the nutritional material. When considering a reusable, washable feed cup, the components can be formed of a dishwasher-safe material. In general, the components of the feed cup 10 can be formed of a moldable polymeric material that is safe when utilized in conjunction with food. By way of example, the various components of the feed cup can be formed of the same or different polymeric materials including, without limitation, poly(vinyl chloride), poly(ethylene), etc. The materials utilized for forming the enteral feed cup can be deemed as suitable for food storage, e.g., suitable for storage of infant formula. Accordingly, the components can be formed so as to be free of any materials that may be allergenic or otherwise present possible dangers. For instance, the components can be formed of materials that are free of biphenol A (BPA free), free of bis(2-ethylhexyl) phthalate (DEHP free), and free of natural rubbers (latex free). The components may be formed of non-polymeric as well, for instance glass or metals (e.g., aluminum).

The components of the enteral feed cup can be formed according to any suitable methodology including, without limitation, injection molding, blow molding, rotomolding, thermoforming, and so forth.

Figure 6:
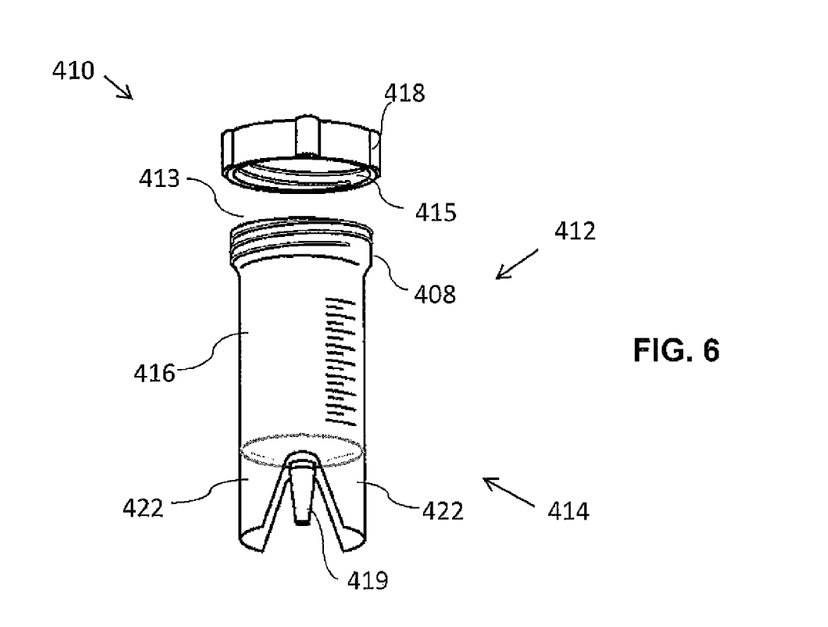
FIG. 6 illustrates another embodiment of an enteral feed cup as disclosed herein.

FIG. 6 illustrates another embodiment of an enteral feed cup 410. As can be seen, in this embodiment the closure 415 includes features 418 in the form of raised ridges for improving the grip of an individual when tightening and loosening the closure 415 on the body 416.

The cup 412 can also include a wider portion 408 on the distal end of the feed cup 413, as shown. The wider portion 408 can be utilized to hang the cup on a stand, discussed further below. For instance, the feed cup can have a diameter that is increased by about 0.25 inches or more, for instance from about 0.25 inches to about 1 inch to form the wider portion 408 on the distal end 412. The wider portion 412 can on the upper half of the body 416, for instance within about two inches of the opening 413, or within about one inch of the opening 413. Though illustrated in FIG. 6 as a widening of the diameter of the body 416, the wider portion 408 can be formed by any suitable design. For example, the wider portion 408 can be formed through the addition of one or more struts, wings, rings, or other extensions from the side of the body 416 so as to form a wider portion on the distal end of the body by which the body may be securely hung in a stand or other brace.

At the proximal end of feed cup 410, the body 416 includes structures 422 that extend from the wall of the body 416 beyond the end of the catheter tip discharge 419. As with the single removable structure 22 of FIG. 1, the multiple structures 422 provide surfaces (i.e., the terminal ends of the structures 422) upon which the enteral feed cup 21 can freely stand on the proximal end 414 as shown. A feed cup such as is illustrated in FIG. 6 that includes integral structures 422 for use in standing the cup 410 on the proximal end can also include a cap (not illustrated) that can cover the catheter tip discharge during transport and/or storage.

Figure 7:
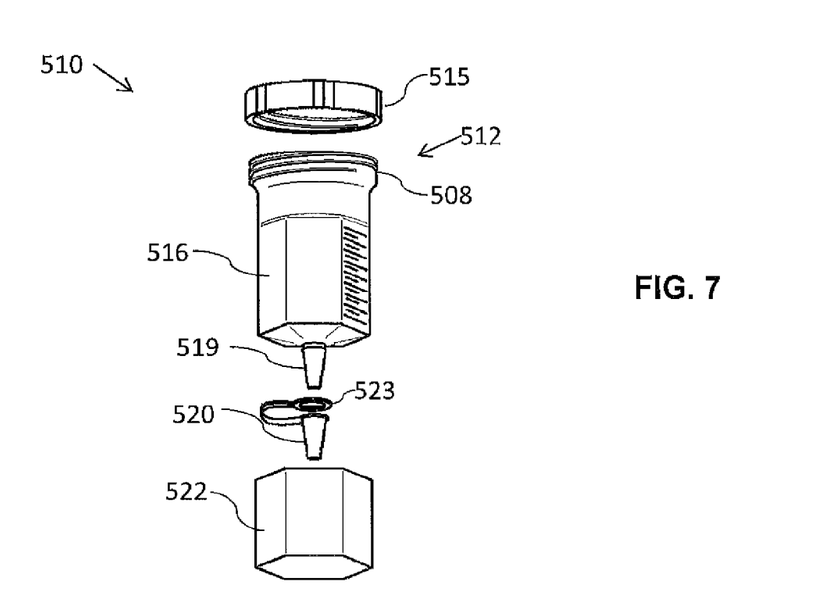
FIG. 7 illustrates another embodiment of an enteral feed cup as disclosed herein.

The enteral feed cup 510 as illustrated in FIG. 7 includes a body 516 and a structure 522 that define a non-circular cross section along a portion of the body length, as shown. The non-circular portion can be beneficial as it can prevent rolling of the feed cup 510 when placed on the side, for instance during storage. As illustrated, in this embodiment the body 516 defines a round diameter at the distal end 512 of the body and the wider portion 508 of the feed cup 510 can thus define a circular cross section. This is not a requirement, however, and the body may define a non-circular cross section along the entire length of the body or only along a portion of the body length.

The catheter tip cover 520 includes a holding ring 523 that can be utilized to tether the catheter tip cover 520 to the body 516 and prevent loss or damage to the tip cover.

The enteral feed cup can be utilized to supply liquid nutrition by either a continuous (slow) feed or bolus (batch) feed, as desired. In a continuous feed, the flow of liquid nutrition is generally established by the use of a pump, e.g., a battery operated pump, while in a bolus feed the flow can be either forced in conjunction with the use of a pump or achieved by gravity.

Figure 8A:
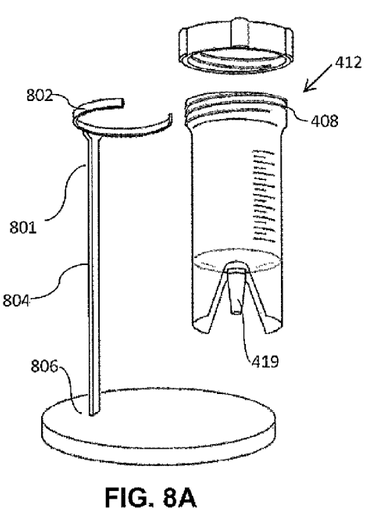
Figure 8B:
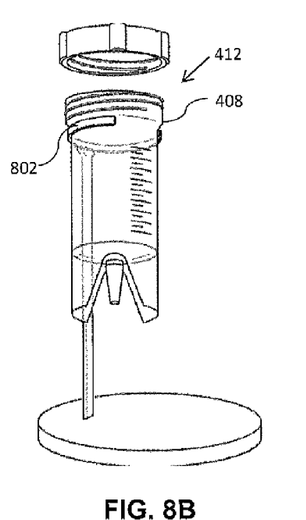

As mentioned, an enteral feed cup can be designed in one embodiment so as to be conveniently held in a stand, for instance a stand that can freely stand on a table top without leaning or tipping. FIG. 8 illustrates a stand 801 that can be utilized in conjunction with enteral feed cup 412. The stand 801 includes a base 806 that can provide stability to the stand 801 both when it is empty as shown in FIG. 8A and following assembly with an enteral feed cup 412 as shown in FIG. 8B. The stand 801 also includes a post 804 and a ring 802. The post 804 can be of a height so as to provide space beneath the discharge tip 419 following assembly of the enteral feed cup 412 with the stand 801 so as to allow for the connection of the tube extension set to the discharge tip 419. The ring 802 can be open as shown in FIG. 8 or can be closed, but in any case can hold the enteral feed cup 412 at the base of the wider portion 408.

Figure 9A:
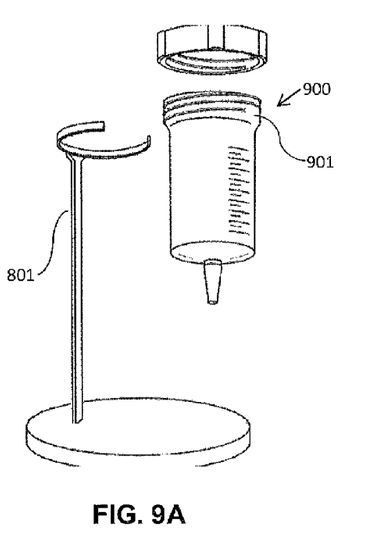
Figure 9B:
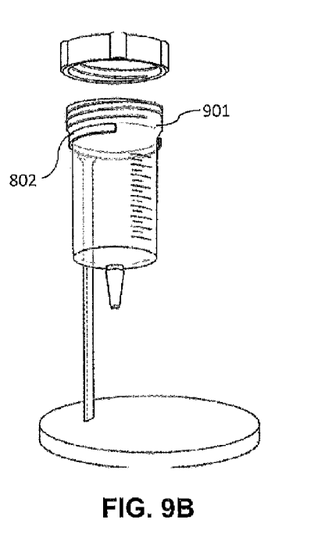

FIG. 9 illustrates the stand 801 in exploded view (FIG. 9A) and following assembly (FIG. 9B) with another enteral feed cup 900. As can be seen, the enteral feed cup 900 includes a wider portion 901 that can be used to hold the enteral feed cup in the stand 801 by use of the ring 802. Of course, utilization of a stand such as is illustrated in FIGS. 8 and 9 is not a requirement of the disclosed systems, and the enteral feed cups disclosed herein can alternatively be simply held or used in conjunction with other bracing mechanisms as are generally known in the art.

The enteral feed cup can be utilized for feeding individuals having any condition that requires enhanced feeding methods such as, without limitation, cancers of the throat or esophagus, dementia, swallowing disorders, cognitive impairments, mechanical obstructions, strokes, eospinhillic esophagusitis, failure-to-thrive, cardiopulmonary disorders, gastrointestinal disorders, and neuromuscular disorders, such as muscular dystrophy, spinal cord defects, or cerebral palsy. In addition, the enteral feed cup can be used on short-term, long-term, or on a permanent basis.

Figure 10:
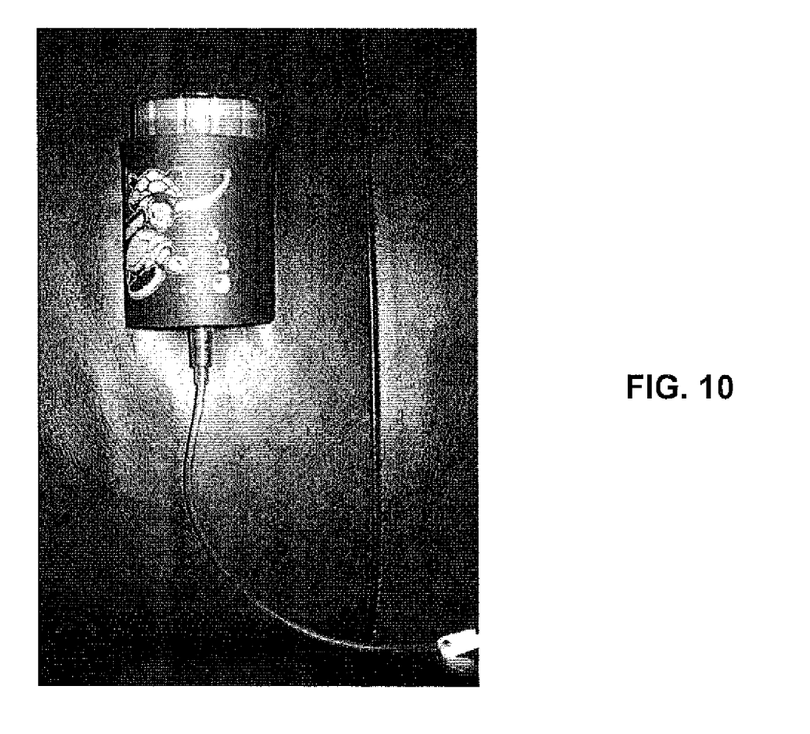
FIG. 10 illustrates an enteral feed cup held in a standard drink holder.
Figure 11:
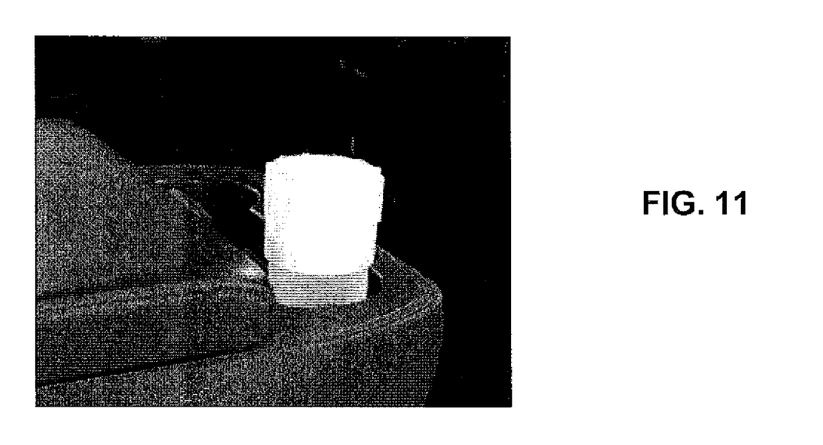
FIG. 11 illustrates an enteral feed cup held in a car cup carrier.

Individuals can accomplish feedings with the enteral feed cup in any location from the comfort of their home to on-the-go. The feeding cup can be utilized, for example in offices, schools, parks, and the like. The beneficial design of the enteral feeding cup can even allow for feedings taking place in locations such as in a car or airplane. The enteral feed cup can be utilized to prepare an amount of nutritional material for an entire feeding cycle in advance and transported as desired. For instance, the size and shape of the enteral feed cup allows for storage in lunch bags, drink holders, or coolers. Moreover, and as illustrated in FIG. 10, as the enteral feed cup can be formed to a size similar to standard drinking cups and bottles, the enteral feed cup can be held in a wrapping, such as a foam holder as is commonly utilized to maintain the temperature of a drink. Due to the convenient size of the enteral feed cup, the feed cup can also be safely and securely held in a car cup holder as illustrated in FIG. 11. This can provide a simply, safe way to transport the enteral feed cups prior to or following use.

The enteral feed cup can be utilized for feedings for adults and children of any age. For example, the enteral feed cup can offer convenience for pediatric feedings and/or medicine dosing. In the past pediatric enteral feedings were difficult with the child often attempting to assist by holding the syringe cup during a gravity bolus feed. In addition to this being difficult for children under any circumstances, many tube-fed children suffer from health concerns such as motor skill delays or physical handicaps, which make holding the syringe impractical. Also, due to the extremely small opening of the typical syringe, it can be difficult (if not impossible) to pour supplemental liquid into the opening without spilling. By use of the disclosed enteral feed cup, an adult can connect the cup to the child's tube without needing the child, a third person, or a stand to hold the syringe. In fact, an adult could place the enteral feed cup on a table top, the child's lap, or any convenient location while connecting to the tube. Following connection, the tube valve can be opened and the closure at the distal end of the feed cup loosened or removed to allow the feeding to begin.

The enteral feed cup can also facilitate pediatric feedings and/or medicine dosing at night, as a caregiver can connect the enteral feed cup to the child's tube in relative darkness without additional aid. Upon removal of the closure at the distal end of the feed cup the feed can begin and be carried out without any refilling of the feed cup during the feeding cycle.

The size and design of the enteral feed cup can improve safety of enteral feedings. For example, as a complete meal and appropriate medicine dosings can be prepared in advance, errors that may otherwise be inadvertently made, for instance at the office or at school, can be avoided. Batching the entire feeding in one container eliminates the need for any refilling during a feeding cycle, which in turn minimizes the risk of errors during the refill (for instance refilling with a different (wrong) liquid). The inherent safety of the enteral feed cup can allow individuals to feel secure, for instance when the user has food allergies.

Busy schedules often dictate that tube feedings be completed on the go. Users of feeding tubes can be very self-conscious, so obviously they don't want to draw attention to the process. Elevating a syringe while pouring liquid into it can certainly draw unwanted notice. By use of the enteral feed cup described herein an individual does not have to elevate the unit until the tube is connected and feeding is ready to begin. To onlookers, it would appear that the user is holding a cup. In fact, standard size soft drink cozies could even be used to camouflage the identity of the feed cup. Use of the enteral feed cup can help boost the esteem and confidence of tube-fed children and adults by providing for less conspicuous public feedings.

The present disclosure may be better understood with reference to the Example presented below.

EXAMPLE

Figure 12A:
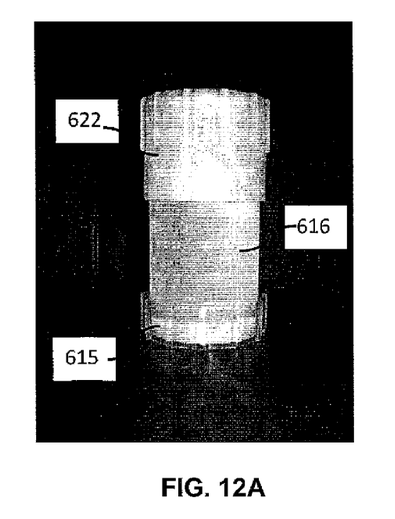
FIGS. 12A-12C are images of an enteral feed cup as described herein.
Figure 12B:
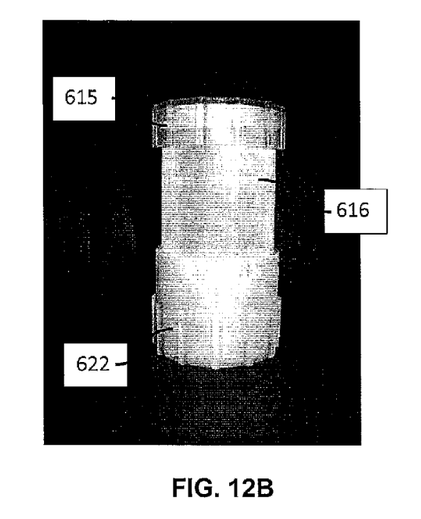
Figure 12C:
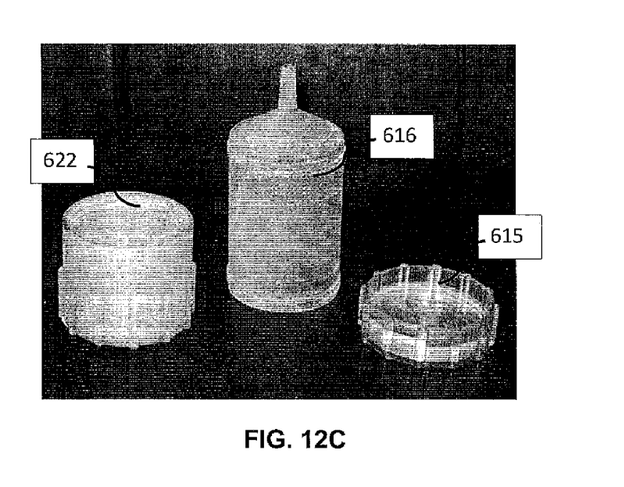

An enteral feed cup was formed, views of which are shown in FIGS. 12A-12C. As can be seen, the enteral feed cup includes a closure 615 that can seal the distal end of the body 16 and a cap 622 that can be located over the proximal end of the body. The flat surfaces on the ends of the closure 615 and the cap 622 allow the enteral feed cup to stand on either end of the cup, as illustrated in FIGS. 6A and 6B. In addition, both the closure 615 and the cap 622 include a series of raised ridges on the circumference, which can aid in loosening and tightening both the cap 622 and the closure 615. As mentioned previously, the raised ridges can also prevent rolling of the cup, for instance while making connections.

It will be appreciated that the foregoing examples, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure which is defined in any following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. An enteral feed cup comprising:
a body having a proximal end and an opposite distal end, the body defining a reservoir to contain a fluid;
a connector at the proximal end;
an opening providing access to the reservoir at the distal end;
a closure that is removably attachable to the distal end of the body, the closure reversibly sealing the distal end of the body with a water-tight seal upon the attachment, the closure including a flat surface, whereupon upon attachment of the closure to the distal end of the body the enteral feed cup is capable of standing on the distal end via the flat surface of the closure, the closure being capable of allowing air flow in and out of the body during use;
the proximal end comprising a structure, the structure providing support such that the enteral feed cup is capable of standing on the proximal end via the structure of the proximal end.

2. An enteral feed cup comprising:
a body having a proximal end and an opposite distal end, the body defining a reservoir to contain a fluid, the body including an upper half that is closer to the distal end than to the proximal end, the proximal end of the body having a cross-sectional dimension, the body including a wider portion, the wider portion having a cross-sectional dimension that is larger than the cross-sectional dimension of the proximal end, the wider portion being on the upper half of the body;
a connector at the proximal end;
an opening providing access to the reservoir at the distal end;
a closure that reversibly seals the distal end of the body with a water-tight seal;
a self-standing bracket, the self-standing bracket including a portion having a cross sectional dimension that is less than the cross sectional dimension of the wider portion of the body such that the self-standing bracket is capable of supporting the body with the wider portion of the body resting on the portion of the self-standing bracket.

3. The enteral feed cup of claim 1, the closure comprising one or more features on a surface of the closure.

4. The enteral feed cup of claim 1, the reservoir having a volume of between about 4 fluid ounces and about 24 fluid ounces.

5. The enteral feed cup of claim 1, wherein the closure can be loosely attached to allow the air flow in and out of the body during use.

6. The enteral feed cup of claim 1, wherein the connector at the proximal end comprises a tip.

7. The enteral feed cup of claim 1, wherein the connector at the proximal end is connectable to a tube.

8. The enteral feed cup of claim 1, wherein the connector is removably attachable to the proximal end of the body.

9. The enteral feed cup of claim 1, wherein the structure at the proximal end is a removable cap.

10. The enteral feed cup of claim 1, wherein the structure at the proximal end extends from a wall of the body and extends beyond an end of the connector.

11. The enteral feed cup of claim 2, the closure comprising one or more features on a surface of the closure.

12. The enteral feed cup of claim 2, the reservoir having a volume of between about 4 fluid ounces and about 24 fluid ounces.

13. The enteral feed cup of claim 2, wherein the closure can allow air flow in and out of the body during use.

14. The enteral feed cup of claim 2, wherein the connector is removably attachable to the proximal end of the body.

15. An enteral feed cup comprising:
a body having a proximal end and an opposite distal end, the body defining a reservoir to contain a fluid;
a connector at the proximal end;
an opening providing access to the reservoir at the distal end;
a closure that reversibly seals the distal end of the body with a water-tight seal;
a tube extension set comprising a component that is removably attachable to the connector;
a cap that is removably attachable to the body, the cap providing a storage location for the tube extension set.

16. The enteral feed cup of claim 15, wherein the cap comprises a surface upon which the enteral feed cup can stand on the proximal end.

17. The enteral feed cup of claim 15, the tube extension set including one or more of an adapter, a clamp, tubing, and a connection member.

18. The enteral feed cup of claim 15, the reservoir having a volume of between about 4 fluid ounces and about 24 fluid ounces.

19. The enteral feed cup of claim 15, wherein the closure can allow air flow in and out of the body during use.

20. The enteral feed cup of claim 15, wherein the connector is removably attachable to the proximal end of the body.

* * * * *